(12) United States Patent
Worley et al.

(10) Patent No.: US 7,384,422 B2
(45) Date of Patent: Jun. 10, 2008

(54) TELESCOPIC, SEPARABLE INTRODUCER AND METHOD OF USING THE SAME

(75) Inventors: Seth J. Worley, Lancaster, PA (US); Paul Kurth, Rancho Palos Verdes, CA (US)

(73) Assignee: Pressure Products Medical Supplies, Inc., Santa Barbara, CA (US)

( * ) Notice: Subject to any disclaimer, the term of this patent is extended or adjusted under 35 U.S.C. 154(b) by 450 days.

(21) Appl. No.: 10/139,554

(22) Filed: May 6, 2002

(65) Prior Publication Data

US 2003/0208220 A1 Nov. 6, 2003

(51) Int. Cl.
*A61B 19/00* (2006.01)

(52) U.S. Cl. ........................................ 606/129; 600/585

(58) Field of Classification Search ................. 606/108, 606/190, 191, 194; 604/96, 104, 107; 600/585
See application file for complete search history.

(56) References Cited

U.S. PATENT DOCUMENTS

| | | | |
|---|---|---|---|
| 4,616,652 A * | 10/1986 | Simpson | ..................... 606/194 |
| 5,190,528 A | 3/1993 | Fonger et al. | |
| 5,715,818 A * | 2/1998 | Swartz et al. | ................ 600/374 |
| 5,897,584 A | 4/1999 | Herman | |
| 6,185,449 B1 * | 2/2001 | Berg et al. | .................. 600/435 |
| 6,277,107 B1 * | 8/2001 | Lurie et al. | .................. 604/528 |
| 6,562,049 B1 * | 5/2003 | Norlander et al. | ........... 606/108 |

* cited by examiner

*Primary Examiner*—Michael J. Hayes
*Assistant Examiner*—Victor Nguyen
(74) *Attorney, Agent, or Firm*—Myers Dawes Andras & Sherman LLP (57) ABSTRACT

An introducer system is used for implantation of pacemaker leads into the venous system of the human heart through the coronary sinus. The system is comprised of three telescopic components, an inner telescoping core, a precurved inner telescoping sheath, and an outer telescoping sheath, introducer, guide or catheter. In an embodiment where a core is used it is torsionally stiff. In an embodiment where no core is used, the inner sheath is torsionally stiff. In either case, the member which is torsionally stiff is torqueable. In general, the inner sheath and outer guide will be both laterally and torsionally flexible, while the core will be torsionally stiff. The core and inner sheath, when curved together in the venous system and proximally coupled, will be sufficiently bound to each other that proximal rotation of the core will be coupled to and cause distal rotation of the inner sheath.

10 Claims, 6 Drawing Sheets

TELESCOPIC, SEPARABLE INTRODUCER AND METHOD OF USING THE SAME

BACKGROUND OF THE INVENTION

1. Field of the Invention

This invention relates to sheaths and introducers, which are utilized in a human heart, which has been altered by heart disease. More particularly, this invention relates to a telescopic peel-away catheter with a core.

2. Description of the Prior Art

The coronary sinus is the largest cardiac vein and serves as a conduit for access to various locations within the heart. Depending on the depth of insertion of the medical device into the coronary sinus, both the left and right atria and the left and right ventricles of the heart can be analyzed. However, introduction of a medical device into the ostium of the coronary sinus is quite difficult as a result of the structure of the heart, the difficulty in locating the coronary sinus using conventional medical technology and the constantly changing shape of the heart while beating as well as the altered anatomy of the heart with cardiomyopathy.

The anatomy of the coronary sinus branch vein presents novel problems for canulation and pacemaker insertion. During pacemaker implantation the delivery system must be steerable to properly locate and insert itself into the ostium of the coronary sinus. Thereafter, the delivery device must have the ability to be steered through a highly branched vasculature to smaller and smaller vessels, yet it must not be so stiff or biased to be traumatic to the vessels. After implantation the delivery system must then leave in place a highly flexible, poorly steerable pacemaker lead.

Figure 1A:
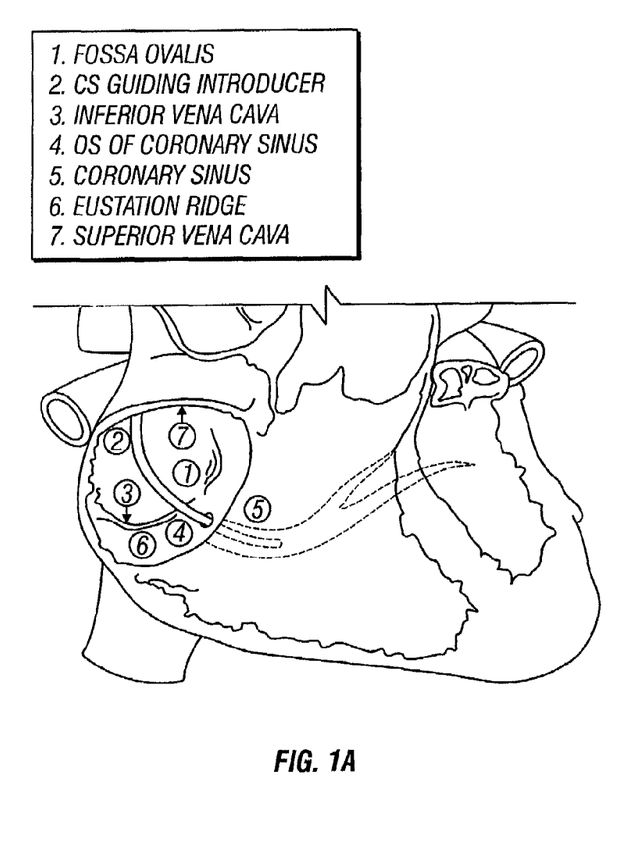
FIG. 1a is a cutaway view of the human heart from the right side showing the coronary sinus guiding introducer placed in the coronary sinus using the superior approach.
Figure 1B:
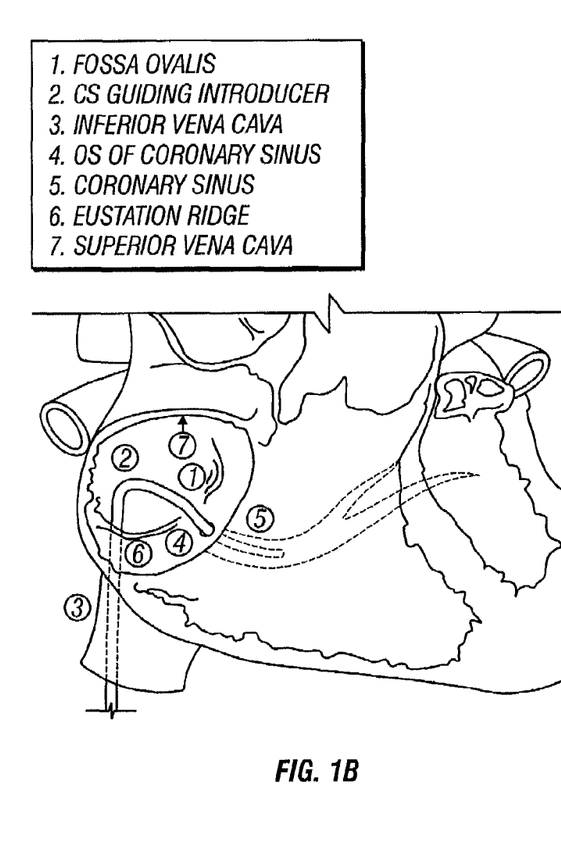
FIG. 1b is a cutaway view of the human heart showing an alternate preferred embodiment of the coronary sinus guiding introducer placed in the coronary sinus using an inferior approach.

Two approaches are commonly used for placement of a medical device within the coronary sinus, an inferior approach from below the heart, and a superior approach from above the heart. In the superior approach, the device is advanced through either the right or left cephalic or right or left subclavian vein through the superior vena cava into the right atrium until it is directed toward the coronary sinus. See FIG. 1a. In the inferior approach, the device is generally advanced through the femoral vein through the inferior vena cava into the right atrium. See FIG. 1b. The tip of the device is then directed toward the ostium of the coronary sinus. The superior approach is the preferred approach and is the approach for which the introducer of the present invention is optimized.

Telescopic catheters are well known and applied to a variety of arterial operations, but never before into the venous system. Typically, one use for such catheters is in the placement of angioplasty balloons in heart arteries. The following United States patents disclosed various forms of dilatation catheters: U.S. Pat. Nos. 3,435,426; 4,271,839; 4,323,071 and 4,338,942. The use of a guiding catheter having a distal tip that can be shaped to facilitate positioning or guiding a catheter into a selected coronary blood vessel is thus well known. Successful angioplasty requires that the balloon of a dilatation catheter be positioned within a stenosis. The more severe the stenosis, the more pressure required to position the dilatation catheter within it. Although very few stenoses within the main coronary artery are so severe as to be impenetrable by a balloon catheter, about 30% of stenoses located in the left circumflex artery cannot be treated with angioplasty. Such is the case because transmission of axial force to the distal end of the catheter from the proximal end is impeded by presence of a sharp bend where the catheter shaft traverses the intersection of the circumflex artery with the main artery.

Thus telescopic catheters have been devised as shown in U.S. Pat. No. 4,616,652 for introducing guide for a balloon catheter. The guide is composed of three parts that are relatively axially movable in telescoping relation to one another. The inner-most part is formed of wire the distal end of which can be selectively deformed to facilitate the manipulation of the distal end through blood vessel intersections. The center or intermediate part, which has a central lumen in which the wire is telescoped, has a tapered distal end and is formed of material possessing sufficient rigidity to be advanced along the wire after the wire is in place, and sufficient flexibility to conform to the wire configuration. The outer part telescopes on to the exterior of the intermediate part. The outer part defines a passage having an inside diameter that is large enough to afford entry of a balloon catheter therethrough. The outside diameter of the intermediate part is less than the inside diameter of the passage so that when the wire and intermediate part are positioned, the outer tube can be advanced therealong.

Thus the telescopic introducer for a dilatation catheter has sufficient flexibility to be manipulated around irregular paths, such as occur within the intersection between the main artery and the left circumflex artery, but has sufficient stiffness or rigidity that it can be moved to a position adjacent a stenosis to be treated by angioplasty. This object is effected by providing an introducer composed of three relatively axially movable parts which are so arranged that the clinician can individually control the relative axial position of each of the parts. The guide wire contained within the innermost guide controls the direction of the intermediate telescoping introducer. The introducers by themselves are not capable of negotiating the branch vessels of the coronary arteries, but instead rely on the navigation of the wire to control the direction for subsequent guides to follow.

Generally in the arterial system shaped sheaths are not used to navigate the branches of the coronary arterial system, but sheaths and catheters are generally placed using a guidewire. The reason for this is that in the high pressure arterial system there is a high probability of the existence of plaque on the artery walls. Any undue disturbance risks the dislodgment of that plaque with the possibility of a resulting heart attack or stroke. However, in the low pressure venous system plaque is not present and the interior vessel walls are smooth. Thus, while a guidewire can also be used in the venous system, the use of shaped sheaths, introducers and catheters which can be steered without a guide wire is safe. To be steered such shaped sheaths, introducers and catheters must be torqueable or rotatable from their proximal end. It is desirable then to have both a radially flexible sheath, introducer and catheter to avoid trauma to the vessel walls and to more easily track in a tortuous or highly branched venous system, while at the same time to be shaped and torqueable. Generally, to be torqueable and radially flexible at the same time meant that the sheath, introducer and catheter had to include a braided reinforcement in or on it. However, a braided sheath, introducer and catheter means greater expense in fabrication of the sheath, introducer and catheter as well as a larger diameter of the sheath, introducer and catheter or a smaller inner diameter of any lumen in the sheath, introducer or catheter.

One prior art approach has been that shown in U.S. Pat. No. 6,185,449 in which a braidless catheter is combined with a solid inner guide 60. While the catheter is thus not torqueable, the inner guide 60 is inserted in a lumen defined within the catheter and the inner guide 60 is torsionally stiff enough to be torqueable. The catheter is hopefully rotated when the inner guide 60 is rotated. However, in this prior art case the inner guide 60 is rendered torqueable simply by having a sufficiently large enough diameter that it is rendered torsionally stiff given the material from which it is made. Since the material is of a uniform extrusion, the flexural characteristics of the core are uniformly soft or rigid. There is nothing in the structure of inner guide 60 which renders it torsionally stiff or imparts to it the necessary varied characteristics of torque versus flexibility needed for steering coronary sinus venous catheters. Such a limitation of the diameter of inner guide 60, then limits the size of the catheters with which it is used to those having larger diameters and particularly larger diameter lumens in them to accept the larger diameter inner guide 60.

Venous coronary sinus procedures or pacemaker implantations, however, require not a distal stiffness to push through a stenosis, but a variable and controllable distal flexibility or softness, torque control as well as specific distal curves. Therefore, some means is needed to adapt telescoping guides or introducers to achieve this different and opposite object from those realized by arterial telescopic introducers.

BRIEF SUMMARY OF THE INVENTION

In the invention once the guiding system is positioned near or into the entrance of the coronary sinus, it can manipulated through tortuous cardiac paths without damage to the vascular tissue. The curve of the telescoping sheath or guides and not a wire is used to canulate the coronary sinus branch vein. As compared to coronary guides this invention does not rely on guide wires to navigate the branching coronary sinus venous anatomy. After branch vein placement the central core of the inner sheath may be conveniently removed leaving the telescoping sheath in the desired location. After delivery of the pacemaker lead the sheath or guide is then removed, sliced open or peeled apart leaving the pacemaker lead in the branch vein of the coronary sinus. The core needed for adequate torque control for sheaths with score lines or lines of weakness requires the core to have very close tolerances with the outer sheath so that the core when placed inside the outer sheath binds the two elements together as though they were one. Proximal locking of the core element with the outer sheath completes the union of the system. The combined peel-away sheath and central braided core element impart the necessary torque as well as the flexibility in the lateral plane. The combined element allows for the peel-away sheath to act as though it were a braided guide.

For purposes of this specification a guide is defined as a reinforced hollow tube which can be torqued such as a braided catheter. A sheath is defined as a non-reinforced hollow tube which has limited ability to be torqued, such as a plastic sheath with score lines extending along its length. The term 'sheath" is defined for the purposes of this application to be an un-reinforced hollow tube. (generally what is often called a sheath, introducer, guide or catheter)omit. A core is defined as an inner, removable, solid or hollow member that imparts torque control to a sheath by virtue of its composite braided design which allows for excellent torque control while still maintaining the soft flex characteristics necessary for atraumatic placement of the sheath.

Thus, the invention can be defined as an introducer system which is used for implantation of pacemaker leads into the venous system of the human heart through the coronary sinus. The system may be comprised of three telescopic components, an inner straight or precurved telescoping core, a straight or precurved inner telescoping sheath or guide, and an outer sheath or guide. In an embodiment where a core is used in the telescoping inner sheath, the core it is torsionally stiff allowing for torque to be transmitted to the inner telescoping sheath. In an embodiment where no core is used, the inner guide is torsionally stiff. This can be achieved by a braid contained in the wall of the guide. In either case, the member which is torsionally stiff is torqueable. In some embodiments, the inner sheath and outer guide will be both laterally and torsionally flexible, while the core or cores will be torsionally stiff. The core and inner sheath, when curved together and the core inserted into the sheath and proximally locked, will be firmly bound to each other so that proximal rotation of the core will be coupled to and cause distal rotation of the inner sheath. The same is true for the core in the outer guiding sheath embodiment.

More specifically, the invention is defined as a telescopic introducer apparatus for use in the coronary sinus venous system of the heart comprising a flexible, elongate, outer guide or sheath; a laterally flexible, elongate, telescopic inner sheath or guide slidingly disposed in the outer guide or sheath. The inner sheath or guide having a prebiased curvature for navigation within the venous system; and a means for rotating the distal end of the inner or outer sheath or guide from a proximal end of the inner or outer sheath or guide so that the inner or outer sheath or guide is steerable within the venous system. In general the outer sheath or guide, inner sheath or guide or both are longitudinally separable, for example by means of longitudinal score line/s or by slicing the guide with a slicer or by propagating a tear along molecular lines of shear.

In one embodiment the means for rotating a distal end of the inner sheath from a proximal end of the inner sheath so that the inner sheath is steerable within the venous system comprises a torsionally stiff core, and wherein the inner sheath is torsionally flexible. The inner sheath may be unreinforced.

In another embodiment the means for rotating a distal end of the inner or outer guide from a proximal end of the inner or outer guide so that the inner guide is steerable within the venous system comprises means for rendering the inner guide torsionally stiff. The means for rendering the inner or outer sheath torsionally stiff comprises braiding incorporated in or on the inner or outer sheath.

The inner sheath or guide has at least one longitudinal lumen defined therethrough adapted for injection of a fluid, such as a contrast agent. The inner sheath or guide may also have at least one longitudinal lumen defined therethrough adapted for disposition of a guide wire therethrough. The telescopic introducer apparatus may further comprise at least one proximal sidearm communicated to the at least one longitudinal lumen and a hemostatic valve coupled to and terminating the sidearm. Both inner sheath or guide as well as outer sheath or guide may contain sidearms for flushing, aspirating or pressure measurement. Both inner and outer guides may contain hemostatic valves. A distal radioopaque section or marker on the inner or outer sheath or guide, or inner core or outer core may be incorporated.

The inner sheath may be preshaped or precurved and comprises a proximal flexible unbiased portion and a distal precurved portion, which has a curvature for optimally steering the inner sheath into the venous system of the heart. In some embodiments the distal precurved portion has a single radius of curvature and a distal most straight portion. The single radius of curvature and the relative length of the distal precurved portion are such that an open curve is obtained, where an open curve is defined as having an angle between the direction of the longitudinal axis of the proximal portion of the inner sheath where it joins the precurved portion and the direction of the longitudinal axis at a distal end of the precurved portion of the inner sheath of more than 90°.

In other embodiments the single radius of curvature and relative length of the distal precurved portion are such that a closed curve is obtained, where a closed curve being defined as having an angle between the direction of the longitudinal axis of the proximal portion of the inner sheath or guide where it joins the precurved portion and the direction of the longitudinal axis at a distal end of the precurved portion of the inner sheath or guide of less than 90°.

In still other embodiments the precurved portion of the inner sheath comprises two curved subportions and a straight subportion therebetween to form a flattened hook. The two curved subportions comprise a proximal curved subportion having a radius of curvature of a first magnitude and a distal curved subportion having a radius of curvature of a second magnitude less than the first magnitude. In the specifically illustrated embodiment the radius of curvature of the first magnitude is approximately 1 inch and where the radius of curvature of the second magnitude is approximately 0.2 to 0.3 inch.

The invention also includes a telescopic introducer for use in the coronary sinus venous system comprising a flexible, elongate, nontorqueable sheath having a longitudinal lumen defined therein, and an elongate, telescopic core slidingly disposed in the lumen of the sheath. The core is structurally reinforced so that it is torsionally stiff while remaining radially flexible by virtue of a structural reinforcement in or on the core. The core is adapted to rotationally couple with the sheath so that a distal end of the sheath is rotated when a proximal end of the core is rotated. In the illustrated embodiment the core is reinforced by a woven braid of reinforcing fibers which is incorporated in or on the core. By creating a core with a non-uniform consistency, such as is generated by weaving a wire or braid around or embedded in a soft or stiff tube one can create a torsionally very rigid core while at the same time having the flex characteristics remain soft and atraumatic The invention further comprises a method for using the sheath and apparatus disclosed above.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The introducer system of the present invention is used for implantation of pacemaker leads into the venous system of the human heart through the coronary sinus. In the illustrated embodiment, the telescopic catheter of FIG. 2, generally denoted by reference numeral 10, is preferably comprised of telescopic components, namely an inner telescoping core 12 the core may extend out the distal end of the sheath, an inner telescoping sheath or guide 14 and an outer telescoping guide or sheath 16. Core 12 may be made of either a nonreinforced plastic extrusion, solid or hollow or of a reinforced material such as a braid and may be of a single durometer or of multiple durometers. In either case, core 12 is torqueable, which means that its proximal end 18 can be rotated by the physician and its distal end 20 will rotate by a corresponding amount. In other words, while core 12 may be laterally flexible, it is torsionally stiff. In general, inner sheath 14 and outer sheath 16 will be both laterally and torsionally flexible. In one embodiment, however, as described below, core 12 may be omitted and inner or outer guide 14 will then be made to be torsionally stiff.

Figure 2:
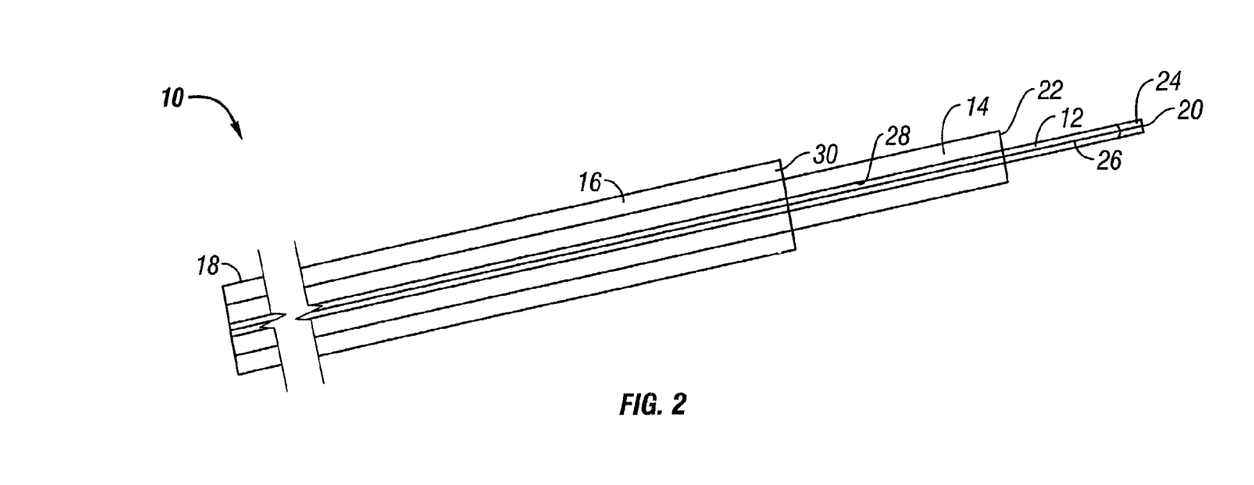
FIG. 2 is a simplified diagrammatic view of one embodiment of the invention in which a torquable telescopic core is used in an unreinforced telescopic inner sheath disposed in a telescopic guide.

In the embodiment where inner sheath 14 is unreinforced and hence not torqueable, it is used with telescopic core 12, which is provided with a structure or reinforcement which renders it torqueable. The frictional coupling or binding between the inner surface of a lumen 26 defined in sheath 14 and the outer surface of core 12 allows the distal end 22 of inner sheath 14 to be rotated when core 12 is proximally rotated also the coupling of the hub and the congruent curves of the core and sheath insure that the combined unit act as a single braided guide. Either core 12 or inner sheath 14 may be biased or shaped according to the coronary sinus application. In the preferred embodiment core 12 includes a braided reinforcement of fibers in or on its body running along its length, which reinforcement renders it torsionally stiff while leaving it radially flexible, even when it has a diameter which is too small to render core 12 torsionally stiff simply by virtue of its size and unreinforced material constituency. In other words, but for the reinforcement core 12 would not be torqueable. Other structural means for reinforcement may be employed in place of braiding. Therefore, it is within the scope of the invention that the invention contemplates the combination of a nontorqueable sheath, introducer, guide or catheter in combination with a structurally reinforced core 12 which is torqueable and which core 12 is used to render the combination torqueable.

Inner sheath or guide 14 is preferably peelable, longitudinally torn apart, or in the case of a reinforced sheath 14, it is sliceable, in which case the sheath or guide may be opened longitudinally. The material of which inner sheath 14 is made may be of such a nature that it tears preferentially along a longitudinal line, or it may be weakened by a defined longitudinal indentation or a longitudinal region of softer or weakened material as is well known to the art. The particular manner by which inner sheath 14 can be separated is not material to the invention as long as the sheath or guide can be removed or peeled off of the pacemaker lead or other device as well as any proximal connectors or fittings that might be in place after the pacemaker lead (not shown) or medical device is implanted as described below. Any structure which will permit the division of the guiding inner and outer sheath or guide 14 into two separate longitudinal halves is within the scope of the invention. In one preferred embodiment, the guiding inner sheath 14 contains a pair of mechanically formed, longitudinally extending zones of reduced thickness defined by internally scored, longitudinally shallow grooves or indentations running throughout the length of the inner sheath 14. These mechanically formed, reduced thickness zones permit the guiding inner sheath 14 to be "split" following use. Alternatively, if the lumen 26 of inner sheath 14 is sufficiently large and the size of the diameter of the medical device passing through the guiding inner sheath 14 is not larger than lumen 26 of inner sheath 14, it is not necessary that the guiding inner or outer sheath or guide 14 be splittable.

The same feature of longitudinal separability is also true for the outer guide 16. In the illustrated embodiment of FIG. 1 inner sheath 14 employs or is used in combination with core 12, which made of a material that allows for torque control. In the embodiment where inner sheath 14 is a guide, i.e. made of a reinforced material, then no inner core 12 is required because inner sheath 14 itself would be torqueable. In this latter embodiment inner sheath 14 would then likely need to be sliced away.

In prior art arterial telescopic catheter systems, such as shown in U.S. Pat. No. 4,616,652, the prior art system requires the telescoping inner tube to track over a wire. This is not the case with telescopic catheter 10 of the invention. While inner sheath or guide 14 may track over a wire, it is specifically designed, by virtue of its unique biased shapes and soft flexible distal end described below to canulate the branch coronary veins without the aid of any wire system. In the embodiment of FIG. 2 the shaped or biased, but non-reinforced sheath 14 will not be torsionally stiff, or at least not all torsionally stiff to be satisfactorily steered by proximal rotations. Such a non-reinforced sheath 14 incorporates a coaxially disposed core 12, which is torsionally stiff and allows for steering of the combined sheath/core unit. The core is what allows the non-reinforced sheath 14 to be torqued or controllably rotated by proximal rotations of the sheath. There is sufficient clearance in a central lumen 28 defined in sheath 14 to allow core 12 to be longitudinally displaced within sheath 14. However, when sheath 14 is allowed to assume its intended biased curvatures, as when distal end 30 of flexible outer sheath 16 is placed at the ostium of the coronary sinus and inner sheath 14 is advanced into the coronary venous system, there is sufficient friction or binding between core 12 and lumen 28 of inner sheath 14, such that inner sheath 14 and core 12 rotate together as core 12 is proximally rotated this is also accomplished by having congruent curves of the core and sheath and proximal locking of the hubs of the core and sheath. The distal curvature of the telescoping inner sheath and congruent curvature of the core along with the frictional coupling or binding between inner sheath and inner core and the proximal locking of the core hub to sheath hub are sufficient to permit reliable rotation of the two as a unit Thus, in the embodiment of FIG. 2 the angulation or bias needed to navigate the coronary venous system is provided in the structure of inner sheath or guide 14 in combination with the core 12, while the means of rotation inner sheath 14, so that it can be steered as desired in the coronary venous system, is provided by the relationship between core 12 and inner sheath 14. In summary, core 12 and sheath 14 can be coupled by: (1) frictional engagement between the outer surface of core 12 and the inner surface of lumen 26 of sheath 14 in which core 12 is inserted; (2) the proximal connection or locking together of the hub of sheath 14 with the hub connected to core 12; and (3) the interference fit between the shaped or biased core 12 and the identically or similarly shaped or biased sheath 14.

Figure 3:
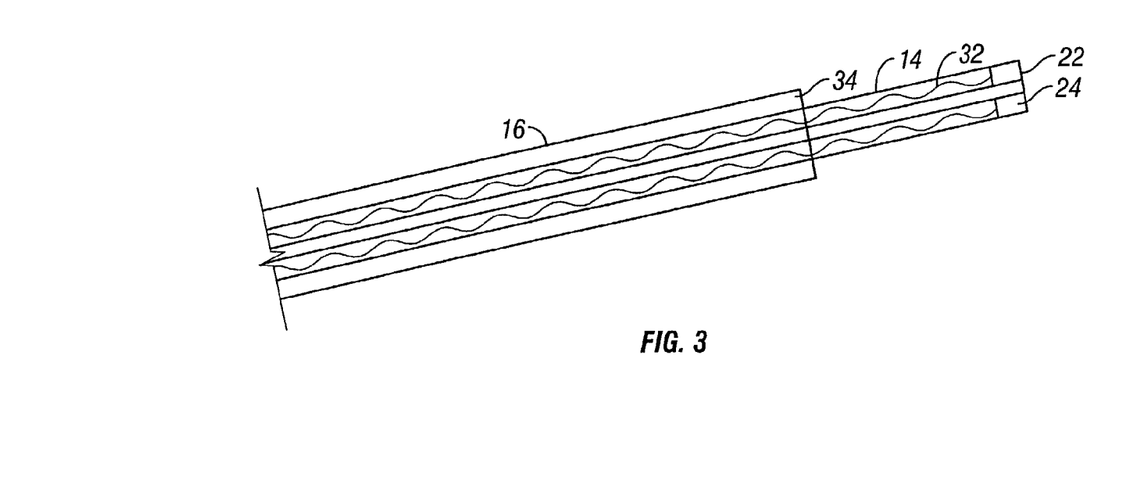
FIG. 3 is a simplified diagrammatic view of another embodiment of the invention in which a torquable reinforced telescopic inner sheath disposed in a telescopic guide.

Alternatively, in the embodiment of FIG. 3 sheath 14 is reinforced with an internal braid or torsionally stiff layer 32 in or on sheath 14, and no core 12 is used, we call this a guide. Reinforced sheath 14 is also provided with the shaped bias needed to be optimally navigated into the coronary sinus venous system. Because of its torsional stiffness, guide 14 can be proximally rotated within lumen 34 in guide 16 with distal end 22 tracking the proximal rotations.

Core 12 extends out a short distance past distal end 22 of sheath 14 and has a soft radio opaque tip 24 for ease of fluoroscopic visualization. Core 12 provides both longitudinal and axial reinforcement as well as containing a central longitudinal lumen 26 for a wire (not shown) and contrast injection. The inner telescoping sheath 14 with an integral core 12 can be placed through the outer sheath or guide 16 and advanced longitudinally and torqued with intermittent small amounts of contrast agent injected to visualize the desired vein branch. Once the desired venous branch is canulated by the protruding core 12, inner sheath 14 is advanced over and past core 12 into the proximal portion of the desired vein. At this point core 12 is removed and pulled out of both the telescoping sheath 14 and the outer guide 16. A wire (not shown) can the be placed if desired for an over-the-wire pacemaker lead or the pacemaker lead can be advanced through telescoping sheath 14 directly into the target vein without the use of a wire.

Of course if telescoping sheath 14 is reinforced it will not require a core 12, but would act as a guide. It would then need to be sliced away once the pacemaker lead is in the desired location. The outer guide or sheath 16 is preferably sliced or peeled away after the telescoping sheath 14 has been removed, but may be removed first. The outer sheath our guide is generally place in the coronary sinus first and the inner telescoping sheath or guide is placed second.

Figure 4:
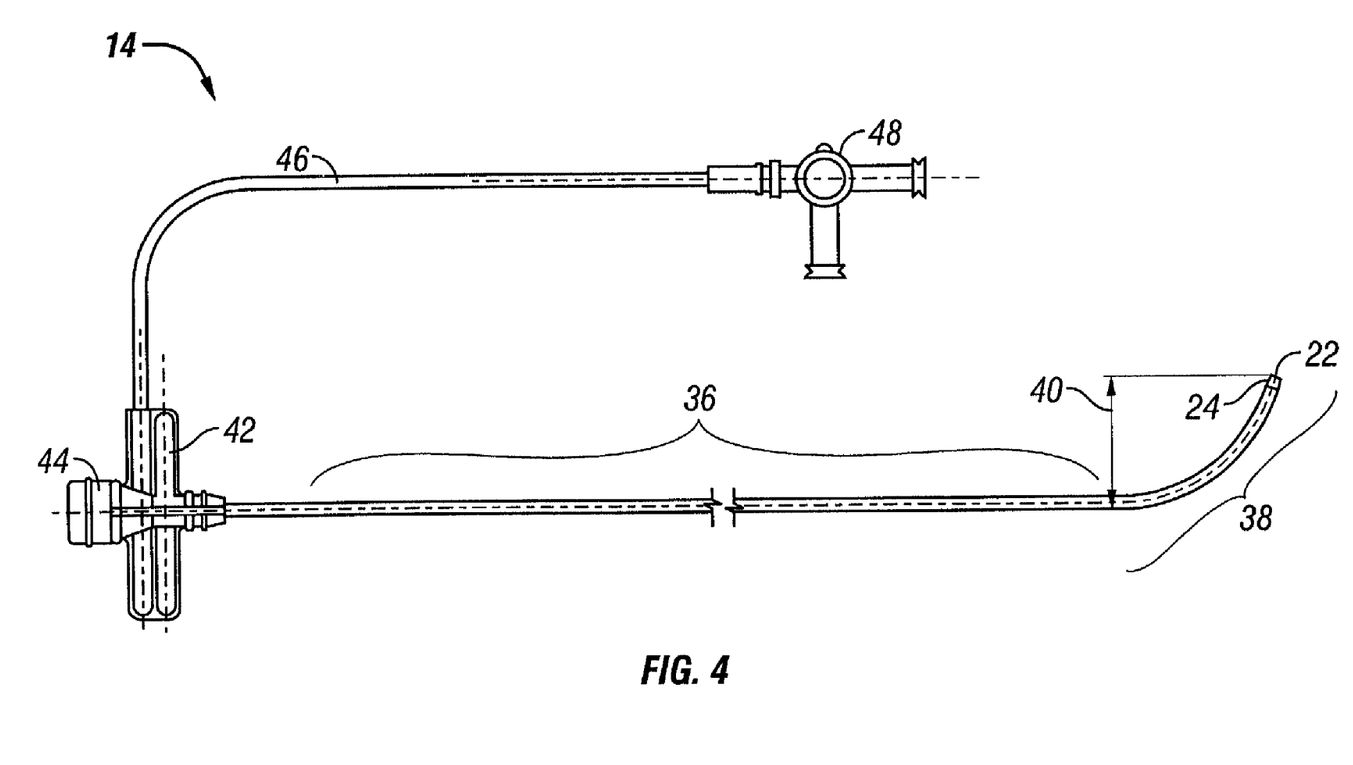
FIG. 4 is a plan view of another embodiment of an introducer formed according to the invention.

FIG. 4 is a plan elevational side view of one embodiment of splittable inner sheath 14 of the invention. A proximal handle 42 is connected to a hub 44. A flexible sidearm tube 46 is communicated to hub 44 and is distally terminated with a hemostatic valve 48 through which contrast agent and other fluids may be injected into lumen 26 of inner sheath 14. Inner sheath 14 may lie in a single plane, such as the plane of FIG. 4. However, it is to be expressly understood that portions of inner sheath 14 may be biased above or below the plane of FIG. 4 to provide an arbitrarily, three dimensionally shaped sheath 14. Portion 36 is defined as the proximal portion of inner sheath 14 and is a generally unbiased, flexible section of inner sheath 14 leading from the percutaneous introduction point into the left cephalic, auxiliary or subclavian veins and through the vasculature leading toward the right atrium and coronary sinus of the heart.

A biased portion 38 of inner sheath 14 forms the distal portion of inner sheath 14, and is either integral with or may be separately fabricated from portion 36. While still being flexible, portion 38 is biased to have a memory so that when the vasculature permits, it tends to assume a prebiased shape as seen in FIG. 4 and described in more detail below. On the other hand, the bias is not so stiff that portion 38 is not easily conformed to the vasculature without risk of injury or trauma.

In general terms, portion 38 has an arcuate bias to form a modified circular or general purpose curvature so that the lateral distance 40 measuring the lateral deflection from the straight line of portion 36 as seen in FIG. 4 is in one embodiment approximately 1.16 inch. Its radius of curvature is approximately 1.31 inch. Inner sheath 14 in this embodiment has a total length of 22.87 inches, and a 7 French inner diameter. However, lateral distance 40 may vary within a range of the illustrated embodiment, namely in a range of 30 to 65 cm.

The distal end 22 is straightened or slightly straightened to at least have less curvature than the remainder of portion 38 or a very low curvature, if any. A perpendicular line to the longitudinal axis of inner sheath 14 at distal end 22 makes an angle with respect to the extended straight line of portion 36 as shown in FIG. 4 of approximately 23°.

Figure 5:
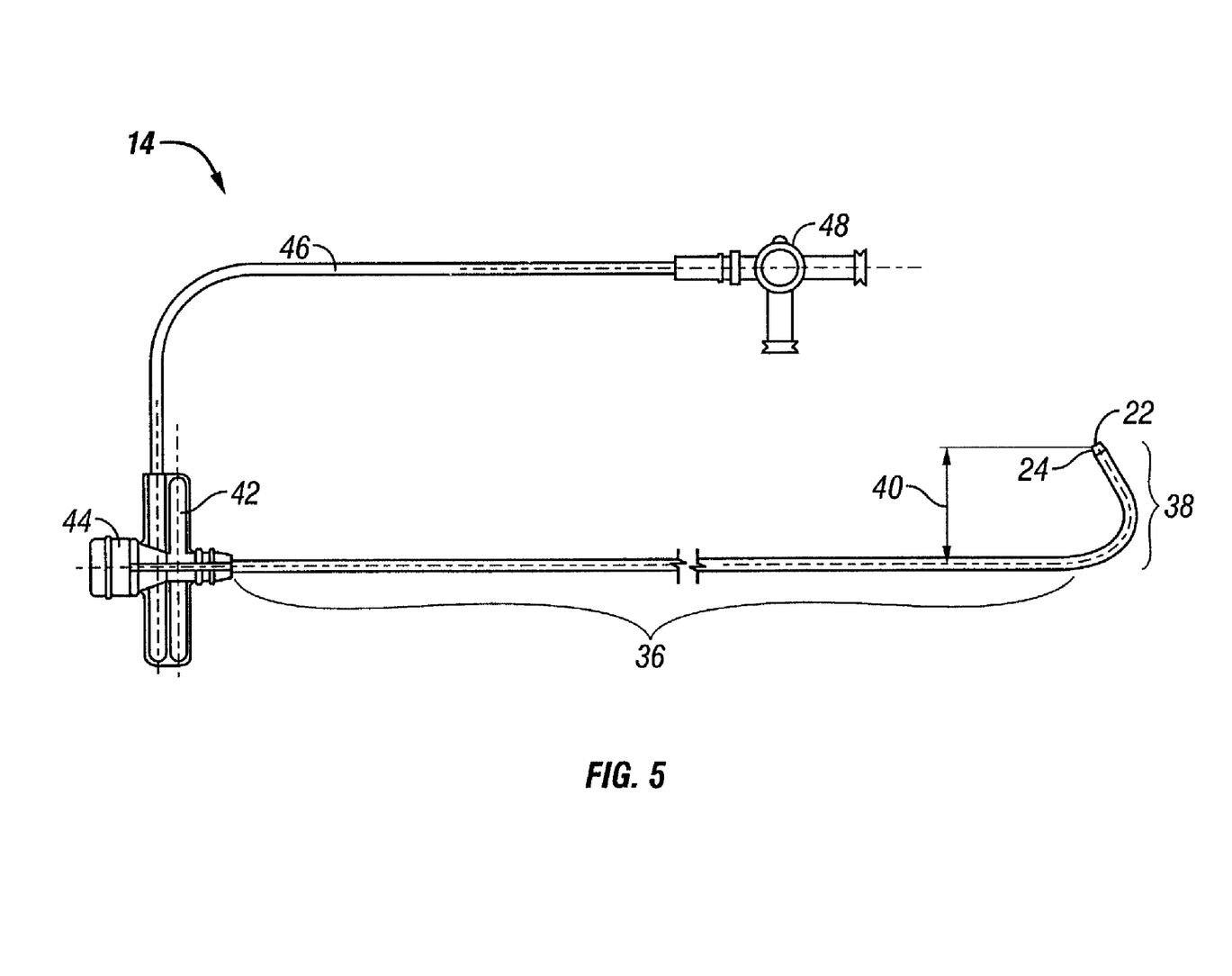
FIG. 5 is a plan view of still another embodiment of an introducer formed according to the invention.

Similarly, in a second embodiment of FIG. 5, what is shown is a plan elevational side view of one embodiment of splittable inner sheath 14 of the invention. Again a proximal handle 42 is connected to a hub 44. A flexible sidearm tube 46 is communicated to hub 44 and is distally terminated with a hemostatic valve 48 through which contrast agent and other fluids may be injected into lumen 26 of inner sheath 14. Inner sheath 14 may lie in a single plane, such as the plane of FIG. 5. However, it is to be expressly understood that portions of inner sheath 14 may be biased above or below the plane of FIG. 5 to provide an arbitrarily, three dimensionally shaped sheath 14. Portion 36 is the defined as the proximal portion of inner sheath 14 and is a generally unbiased, flexible section of inner sheath 14 leading from the percutaneous introduction point into the left cephalic, auxiliary or subclavian veins and through the vasculature leading toward the atrium and coronary sinus of the heart.

A biased portion 38 of inner sheath or guide 14 forms the distal portion of inner sheath 14, and is either integral with or may be separately fabricated from portion 36. While still being flexible, portion 38 is biased to have a memory so that when the vasculature permits, it tends to assume a prebiased shape as seen in FIG. 5 and described in more detail below. On the other hand, the bias is not so stiff that portion 38 is not easily conformed to the vasculature without risk of injury or trauma.

In general terms, portion 38 has an arcuate bias to form a modified hooked or acute curvature so that the lateral distance 40 measuring the lateral deflection from the straight line of portion 36 as seen in FIG. 5 is in this embodiment approximately 1.12 inch. The radius of curvature of portion 38 is approximately 0.49 inch. Inner sheath 14 in this embodiment has a total length of 22.87 inches and a 7 French inner diameter. However, lateral distance 40 may vary within a range of the illustrated embodiment, namely in a range of 35 to 65 cm.

The distal end 22 is again straightened or slightly straightened to at least have less curvature than the remainder of portion 38 or a very low curvature, if any. In the embodiment of FIG. 5 the straightened distal segment of portion 38 is approximately 0.40 inch long. The longitudinal axis of inner sheath or guide 14 at distal end 22 makes an inner angle with respect to the straight line of portion 36 as shown in FIG. 5 of approximately 58°.

Figure 6:
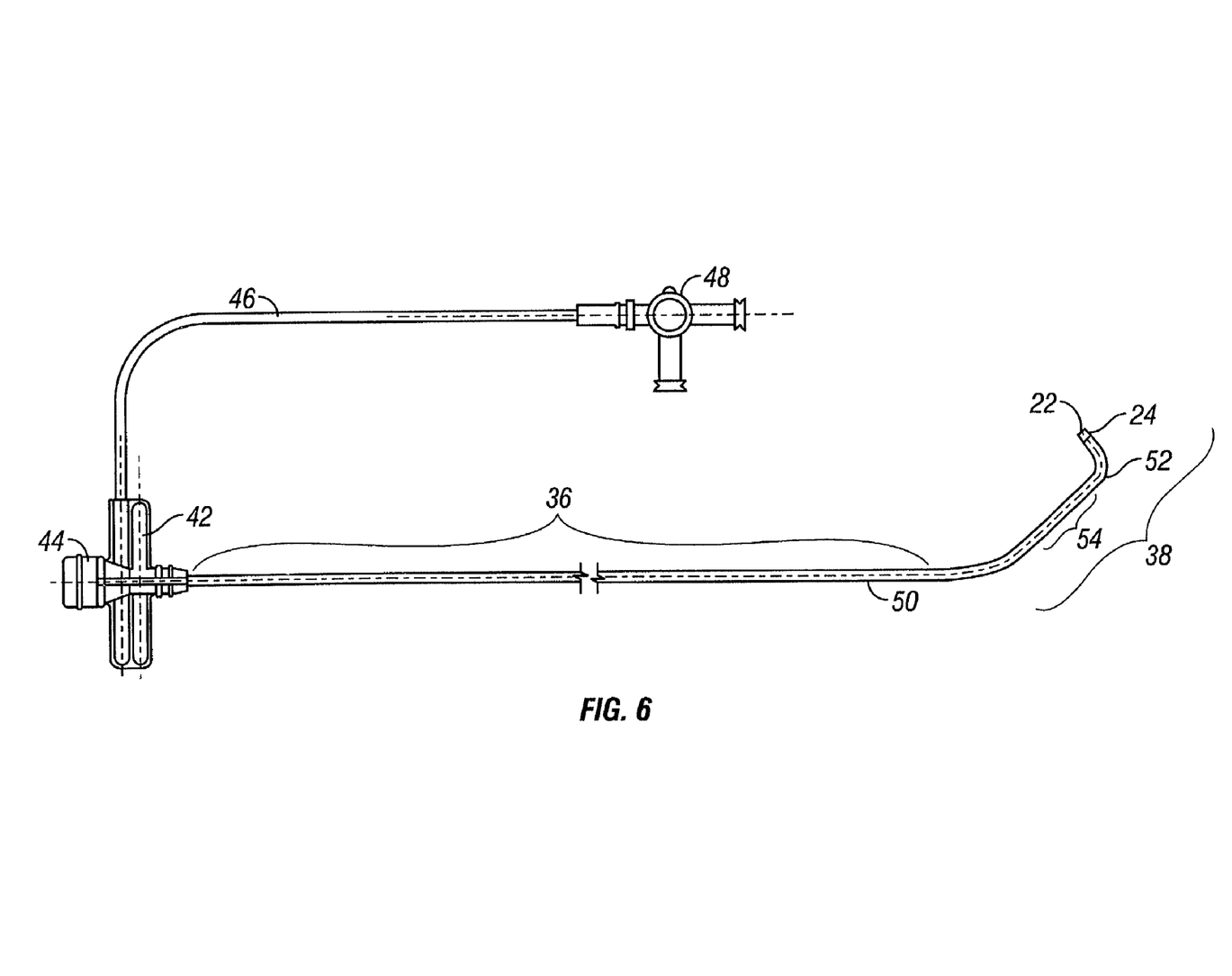
FIG. 6 is a plan view of yet another embodiment of an introducer formed according to the invention.

Still further, in a third embodiment of FIG. 6, what is shown is a plan elevational side view of one embodiment of splittable inner sheath or guide 14 of the invention. Again a proximal handle 42 is connected to a hub 44. A flexible sidearm tube 46 is communicated to hub 44 and is distally terminated with a hemostatic valve 48 through which contrast agent and other fluids may be injected into lumen 26 of inner sheath 14. Inner sheath 14 may lie in a single plane, such as the plane of FIG. 6. However, it is to be expressly understood that portions of inner sheath 14 may be biased above or below the plane of FIG. 6 to provide an arbitrarily, three dimensionally shaped sheath 14. Portion 36 is the defined as the proximal portion of inner sheath 14 and is a generally unbiased, flexible section of inner sheath 14 leading from the percutaneous introduction point into the left auxiliary subclavian vein and through the vasculature leading toward the atrium of the heart.

A biased portion 38 of inner sheath or guide 14 forms the distal portion of inner sheath or guide 14, and is either integral with or may be separately fabricated from portion 36. While still being flexible, portion 38 is biased to have a memory so that when the vasculature permits, it tends to assume a prebiased shape as seen in FIG. 6 and described in more detail below. On the other hand, the bias is not so stiff that portion 38 is not easily conformed to the vasculature without risk of injury or trauma.

In general terms, portion 38 has an arcuate bias to form a modified flattened portion, so that the lateral distance 40 measuring the lateral deflection from the straight line of portion 36 as seen in FIG. 6 is in this embodiment approximately 1.47 inch. The more proximal radius of curvature 50 of portion 38 is approximately 1.06 inch. Distal to curvature 50 is a straight portion 54 of length 0.88 inch. Straight portion 54 is then followed by a second and more distal radius of curvature 52 of portion 38, which is approximately 0.26 inch.

Inner sheath or guide 14 in this embodiment has a total length of 22.87 inches and a 7 French inner diameter. However, lateral distance 40 may vary within a range of the illustrated embodiment, namely in a range of 35 to 65 cm.

The distal end 22 is again straightened or slightly straightened to at least have less curvature than the remainder of portion 38 or a very low curvature, if any. The longitudinal axis of inner sheath 14 at distal end 22 makes an outer angle with respect to the extended straight line of portion 36 as shown in FIG. 6 of approximately 47°.

Figure 7:
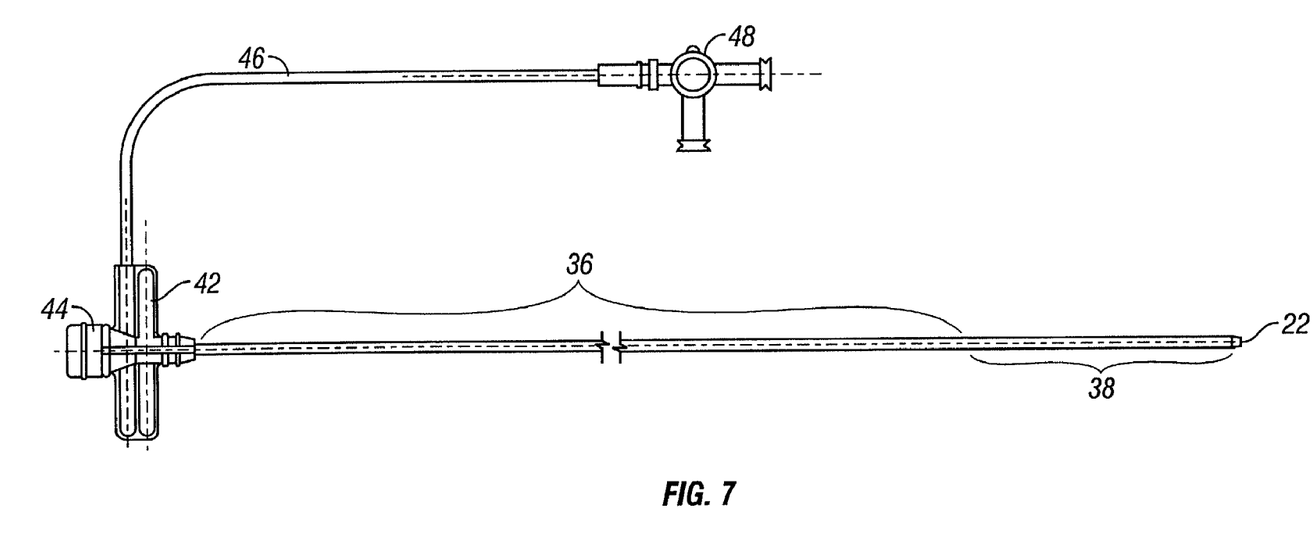
FIG. 7 is a plan view of an embodiment of the invention where the distal portion of the introducer is straight.

FIG. 7 is a plan view of another embodiment of the invention similar to that of FIGS. 4-6 except that distal portion 38 is straight instead of the various curved shapes described above. Thus, distal portion 38 is essentially a continuation of straight proximal portion 36.

Inner sheath or guide 14 may be made of any biocompatible material suitable for use in humans which has a memory or permits distortion from and substantial return to the desired three dimensional shape, such as polyethylene or polyurethane. As is conventional the distal tip 22 of the guiding inner sheath 14 may be made of a more pliable, more compressible material, than the remaining length of the coronary sinus guiding inner sheath or guide 14 to prevent damage to the vasculature and the coronary sinus when in use.

For the purpose of illustration and not limitation, the internal diameter of the guiding inner sheath or guide 14 may vary from about 4 to about 16 French (1 French equals ⅓ of a millimeter). The precurved guiding inner sheath or guide 14 of the invention may also be multi-lumened. According to conventional design principles, the structure of inner sheath 14 may be modified to permit the presence of an inflatable balloon near or at its distal tip or electrodes for sensing or ablation.

Variations in size and shape of the guiding inner sheath or guide 14 are intended to encompass pediatric uses for the guiding introducer of the present invention, although the preferred uses are in adult human hearts. It is well recognized that pediatric uses may require reductions in size of the various portions of the inner sheath 14, in particular shortening the first portion 36, with a proportional reduction in the height, arc and length of curved distal portion 38 of the guiding inner sheath 14, which may extend the lower limits of the specific ranges of the above parameters from those explicitly recited below. In addition, variations in size or shape are also intended to encompass specialized situations that sometimes occur in patients with enlarged or rotated hearts.

The guiding inner sheath or guide 14 can be used to introduce a number of different types of medical instruments into the body through its lumen including a permanent or temporary pacemaker lead, a defibrillator lead, ablation or sensing catheters or any such medical devices that will find use if placed within the coronary sinus. These other uses are well known in the industry and are within the contemplation of the present invention.

The telescoping delivery system of the invention was demonstrated for difficult left ventricular pacing leads. The telescoping delivery system was utilized in 35 cases where the standard approach was unsuccessful. For direct lead delivery, either a SAFESHEATH® CSG (55) with standard interventional guides (15 cases), or a SS®, ATTAIN 6218®, 5 Fr diagnostic catheter and guide wire combination (10 cases) was used. For guide wire delivery, a 5 Fr IMA® or RCA® diagnostic catheter inserted through the guide directed the wire into the target vein. Lead delivery was successful in 33 cases. Therefore, it can be concluded that a telescoping delivery system constructed from available sheaths, guides and diagnostic catheters achieved successful implantation to a lateral wall target vein in 94% (33/35) of patients where standard methods had previously failed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

For example, features of this guiding inner sheath or guide 14 include its unique shape, but may also incorporate a sliceable, peelable or splittable structure, increased stiffness to minimize compression when positioned in tight bends, radioopaque tip sections or markers, balloons and vents according to conventional design principles.

Notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

The invention claimed is:

1. An introducer telescopically disposable in an elongate, outer introducer for use in introducing an endovascular instrument comprising:

a longitudinally separable, inner sheath disposable through the outer introducer, the inner sheath having a prebiased shape of its distal portion for navigation into the coronary sinus branch veins, wherein the inner sheath is arranged and configured to allow introduction of the endovascular instrument into a selected location within the coronary sinus branch veins where the inner sheath comprises a proximal flexible unbiased portion and where the distal portion, which has a shape for optimally steering the inner sheath into a selected branch of the coronary sinus venous system of the heart, wherein the distal shape is characterized by a single radius of curvature and a distal most straight portion, and wherein the inner sheath has a longitudinal axis and the single radius of curvature and relative length of the distal precurved portion are such that an open curve is obtained, an open curve being defined as having an angle between the direction of the longitudinal axis of the proximal portion of the inner sheath where it joins the precurved portion and the direction of the longitudinal axis at a distal end of the precurved portion of the inner sheath of more than 90°, the proximal portion and distal portion lying in a common plane.

2. The introducer of claim 1 further comprising a straight distal tip portion extending from the curved distal portion.

3. An introducer telescopically disposable in an elongate, outer introducer for use in introducing an endovascular instrument comprising:

a longitudinally separable, inner sheath disposable through the outer introducer, the inner sheath having a prebiased shape of its distal portion for navigation into the coronary sinus branch veins, wherein the inner sheath is arranged and configured to allow introduction of the endovascular instrument into a selected location within the coronary sinus branch veins, where the inner sheath comprises a proximal flexible unbiased portion and where the distal portion, which has a shape for optimally steering the inner sheath into a selected branch of the coronary sinus venous system of the heart, and where the precurved portion of the inner sheath comprises two curved subportions and a straight subportion therebetween of form a flattened hook.

4. The telescopic introducer of claim 3 where the two curved subportions comprise a proximal curved subportion having a radius of curvature of a first magnitude and a distal curved subportion having a radius of curvature of a second magnitude less than the first magnitude.

5. The telescopic introducer of claim 4 where the radius of curvature of the first magnitude is approximately 1 inch and where the radius of curvature of the second magnitude is approximately 0.2 to 0.3 inch.

6. A longitudinally separable, inner sheath disposable through an outer introducer for use in introducing an endovascular instrument into coronary sinus branch veins of a heart, the inner sheath comprising:

a flexible unbiased proximal portion; and a curved distal portion adapted for navigation into the coronary sinus branch veins for introducing the endovascular instrument into a selected location within the coronary sinus branch veins, wherein the distal portion extends from the proximal portion and has a shape characterized by a single radius of curvature, and a distal tip, and a length, the length of the distal portion having a magnitude such that the tangent to the distal tip intersects a line extended from the proximal portion with an interior angle 90° or more tending to define an open curve, the proximal portion and distal portion lying in a common plane.

7. The longitudinally separable, inner sheath of claim 6 where the relative length of the distal portion has a magnitude such that the tangent to the distal tip intersects a line extended from the proximal portion with an interior angle in the range of 90°–170°.

8. A longitudinally separable, inner sheath disposable through an outer introducer for use in introducing an endovascular instrument into coronary sinus branch veins of a heart, the inner sheath comprising:

a flexible unbiased proximal portion; and a curved distal portion adapted for navigation into the coronary sinus branch veins for introducing the endovascular instrument into a selected location within the coronary sinus branch veins, wherein the distal portion extends from the proximal portion and has a shape characterized by a single radius of curvature, a distal tip, and a length, the length of the distal portion having a magnitude such that the tangent to the distal tip intersects a line extended from the proximal portion with an interior angle 90° or less tending to define a closed curve, the proximal portion and distal portion lying in a common plane.

9. The longitudinally separable, inner sheath of claim 8 where the relative length of the distal portion has a magnitude such that the tangent to the distal tip intersects a line extended from the proximal portion with an interior angle in the range of 0°–90°.

10. A longitudinally separable, inner sheath disposable through an outer introducer for use in introducing an endovascular instrument into coronary sinus branch veins of a heart, the inner sheath comprising:

a flexible unbiased proximal portion; and a curved distal portion adapted for navigation into the coronary sinus branch veins for introducing the endovascular instrument into a selected location within the coronary sinus branch veins, wherein the distal portion extends from the proximal portion and has a shape characterized by a single radius of curvature, a distal tip, and a relative length, the relative length of the distal portion having a magnitude such that the tangent to the distal tip intersects a line extended from the proximal portion with an exterior angle in the range of 10°–180°, the proximal portion and distal portion lying in a common plane.

* * * * *